(12) United States Patent
Wang et al.

(10) Patent No.: US 11,786,267 B2
(45) Date of Patent: Oct. 17, 2023

(54) FREQUENCY CONTROL METHOD AND SYSTEM FOR ULTRASONIC SURGICAL TOOL

(71) Applicant: INNOLCON MEDICAL TECHNOLOGY (SUZHOU) CO., LTD., Suzhou (CN)

(72) Inventors: Fuyuan Wang, Suzhou (CN); Zhenzhong Liu, Suzhou (CN); Zhongyu Yan, Irvine, CA (US); Wei Luo, Suzhou (CN)

(73) Assignee: INNOLCON MEDICAL TECHNOLOGY (SUZHOU) CO., LTD., Suzhou (CN)

( * ) Notice: Subject to any disclaimer, the term of this patent is extended or adjusted under 35 U.S.C. 154(b) by 893 days.

(21) Appl. No.: 16/635,930

(22) PCT Filed: Jul. 2, 2018

(86) PCT No.: PCT/CN2018/093989
§ 371 (c)(1),
(2) Date: May 13, 2020

(87) PCT Pub. No.: WO2019/024637
PCT Pub. Date: Feb. 7, 2019

(65) Prior Publication Data
US 2020/0297375 A1 Sep. 24, 2020

(30) Foreign Application Priority Data

Aug. 3, 2017 (CN) .......................... 201710656464.1
Feb. 27, 2018 (CN) .......................... 201810159303.6

(51) Int. Cl.
*A61B 17/32* (2006.01)
*A61B 17/00* (2006.01)

(52) U.S. Cl.
CPC .................. *A61B 17/320068* (2013.01); *A61B 2017/00141* (2013.01)

(58) Field of Classification Search
CPC .. A61B 17/320068; A61B 2017/00141; A61B 17/32008; A61B 2017/320069;
(Continued)

(56) References Cited

U.S. PATENT DOCUMENTS 6,480,796 B2   11/2002   Wiener
2017/0072226 A1*  3/2017   Matsui .................. B06B 1/0253

FOREIGN PATENT DOCUMENTS

CN        103567134 A      2/2014
CN        104252146 A     12/2014
(Continued)

*Primary Examiner* — Antony M Paul
(74) *Attorney, Agent, or Firm* — SEED INTELLECTUAL PROPERTY LAW GROUP LLP

(57) ABSTRACT

A frequency control method and system for an ultrasonic surgical tool. The frequency control method for an ultrasonic tool comprised: obtaining a maximum value of a phase difference between an operating voltage and an operating current of the ultrasonic surgical tool; determining whether the maximum value is less than zero, so as to obtain a first determination result; if the first determination result indicates that the maximum value is not less than zero, adjusting an operating frequency of the ultrasonic surgical tool to a frequency corresponding to the phase difference to zero; if the first determination result indicates that the maximum value is less than zero, subtracting a preset value from the maximum value to obtain a phase lock point; and adjusting, according to the phase lock point, the operating frequency of the ultrasonic tool. The frequency control method for an ultrasonic surgical tool solves a problem in which, in some situations where the phase of a self-resonant frequency does not exceed 0, ultrasonic surgical tools fail to operate nor- (Continued)

mally, or operate inefficiently, thereby improving operation efficiency and stability of ultrasonic surgical tools.

10 Claims, 6 Drawing Sheets

(58) Field of Classification Search
CPC ........... A61B 2017/00106; A61B 2017/00017; A61B 2017/00398; A61B 2017/320074; A61B 2018/00827; A61B 2018/00892; A61B 34/30; A61B 18/1206; A61F 9/00745; H02P 27/00; H02P 27/02; H02P 27/08; H02P 27/085; H02P 21/22; H02P 21/14; H02P 23/00; H02P 23/08; H02P 1/00; H02P 1/30; H02P 1/52
See application file for complete search history.

(56) References Cited

FOREIGN PATENT DOCUMENTS

| | | |
|---|---|---|
| CN | 104772450 A | 7/2015 |
| CN | 205411229 U | 8/2016 |
| EP | 1199110 A2 | 4/2002 |

* cited by examiner

FREQUENCY CONTROL METHOD AND SYSTEM FOR ULTRASONIC SURGICAL TOOL

BACKGROUND

Technical Field

The invention includes frequency controlling field, especially, a frequency controlling method and system of ultrasonic surgical instrument.

Description of the Related Art

Ultrasonic surgical instrument, like ultrasonic scalpel, phacoemulsification, and ultrasonic bone scalpel. The application of these instruments has been about 20 years. Comparing with other surgical system, these ultrasonic surgical instruments have many advantages. For instance, the ultrasonic scalpel has the advantages of less smoke, larger surgical vision, less thermal damage, simultaneous cutting, coagulation and separation, no electrical damage, self-cleaning and less sticking with tissue.

Ultrasonic surgical instrument, like ultrasonic scalpel, comprises ultrasonic generator, ultrasonic handpiece and ultrasonic blade; the ultrasonic generator is an electric signal source which is used to drive handpiece and blade and the blade acts on the tissue to achieve cutting and coagulation effect; this kind of cutting needs high frequency, like 55 KHz, and large vibration amplitude, like 50-100 um; the resonant frequency is easy to drift by impedance and temperature. For the high efficiency of the instrument, the driving frequency should be put at resonance around, which requires the frequency tracking function of the instrument.

When the system works at the resonant frequency, the phase difference of current and voltage of the instrument is zero. Normally, for the best efficiency, the phase locking point is set at zero. The frequency tracking function is usually the ability to track zero phase. But in some cases, the system doesn't exist in the zero phase. For example, in the condition of high impedance, the phase difference at resonance is lower than zero and working around a non-zero phase point may be still a good solution. When the system has the zero phase, but still leaving the system to work in the non-zero phase point makes the system inefficient.

BRIEF SUMMARY

Disclosed herein is a method and system of controlling frequency of an ultrasonic surgical instrument, in order to solve the problem of the low efficiency and instability of the surgical instrument, when the phase at the resonance frequency is less than zero.

For this purpose, the invention offers several embodiments:
  A method of controlling frequency of the ultrasonic surgical instrument includes:
    Obtain the maximum phase difference of the current and voltage of the ultrasonic surgical instrument;
    Obtain the first determination result, by checking whether the maximum value is less than zero;
    When the maximum value of the first determination result is not less than zero, tune the frequency of the ultrasonic surgical instrument to the frequency of zero phase difference;
    When the maximum value of the first determination result is less than zero, tune the frequency of the ultrasonic surgical instrument to the frequency which comes from subtracting a presetting value from the maximum value.
  Optionally, obtain the phase locking point from subtracting a presetting value from the maximum value, including:
  According the phase locking formula:

$$ph\_lock = ph\_now - ph\_delta \quad (1)$$

to calculate phase locking point, where, ph_lock is phase locking point, ph_now is the maximum phase difference, ph_delta is first presetting value.
  Optionally, ph_delta is 0-10 degree.
  Optionally, after tuning the frequency of surgical instrument according the phase locking point, including:
    Obtain the current of surgical instrument;
    Calculate the theoretical phase difference according to the current;
  Tune the frequency of surgical instrument according to the theoretical phase difference.
  Optionally, calculate the theoretical phase difference according working current, including:
  According to the formula:

$$ph\_max = a*current + b \quad (2)$$

Calculate maximum phase difference, where, ph_max is theoretical phase difference, current is working current, a and b are known coefficients.
  Optionally, tune the frequency of surgical instrument according to theoretical maximum phase difference, including:
    Let ph_max=ph_now, calculate the second phase difference according to the phase locking point formula;
    When the second determination result is less than zero, tune the frequency of the surgical instrument to the frequency of the second phase difference;
    When the second determination result is no less than zero, tune the frequency of the surgical instrument to the frequency of zero phase difference.
  Optionally, tune the frequency of the surgical instrument according to the maximum phase difference, including:
    Obtain the third determination result according to if the theoretical maximum phase difference is less than zero;
    When the third determination result is less than zero, maintain the frequency of the surgical instrument;
    When the third determination result is no less than zero, tune the frequency of the surgical instrument to the frequency of zero phase difference.
  A method of controlling frequency of an ultrasonic surgical instrument includes:
    Obtain the phase difference of current and voltage of surgical instrument; Obtain the first determination result according to if the maximum value is less than zero;
    When the maximum value of the first result is less than zero, increasing the current of surgical instrument and obtain the voltage value; when the voltage is higher than nominal voltage level, stop increasing the current; obtain the phase locking point from subtracting a presetting value from the maximum value; tune the frequency according to the phase locking point;

When the first determination result is no less than zero, tune the frequency of the surgical instrument to the frequency of zero phase difference.

A system of controlling frequency of an ultrasonic surgical instrument includes:

Acquisition circuitry, for obtaining the phase difference of the current and voltage of the surgical instrument;

Determination circuitry, for determining if the maximum value is less than zero and obtaining the first determination result; The first tuning circuitry, when the result of first determination is no less than zero, tune the frequency of surgical instrument to the frequency of zero phase difference;

The second tuning circuitry, when the result of first determination is less than zero, tune the frequency to the point coming from subtracting a presetting value from maximum value; tune the frequency of the surgical instrument according to the phase locking point.

A system of controlling frequency of an ultrasonic surgical instrument includes:

Acquisition circuitry, for obtaining the phase difference of the current and voltage of the surgical instrument;

Determination circuitry for determining if the maximum value is less than zero and obtaining the fourth determination result;

The first tuning circuitry. When the maximum value of the first result is less than zero, increasing the current of surgical instrument and obtain the voltage value; when the voltage is higher than nominal voltage level, stop increasing the current; obtain the phase locking point from subtracting a presetting value from the maximum value; tune the frequency according to the phase locking point;

The second tuning circuitry. When the first determination result is no less than zero, tune the frequency of the surgical instrument to the frequency of zero phase difference.

According to the embodiments provided in the invention, the invention disclosed below technical benefits:

The invention offers the method of controlling frequency of the ultrasonic surgical instrument. When the maximum phase difference value of the current and voltage is less than zero, preset a phase locking point below the maximum value and tune the frequency to the phase locking point. This method resolves the problem of the inability and low efficiency of the surgical instrument, when the phase difference at the resonant frequency is less than zero, which improves the stability and efficiency of the instrument.

The invention offers the method of controlling frequency of the ultrasonic surgical instrument. When the maximum phase difference value of the current and voltage is less than zero, increase the current of surgical instrument to increase the phase difference of the current and voltage to approach or exceed zero. This method resolves the problem that the inability and low efficiency of the surgical instrument, when the phase of resonant frequency is less than zero, which improves the stability and efficiency of the instrument.

BRIEF DESCRIPTION OF THE SEVERAL VIEWS OF THE DRAWINGS

The described embodiments, however, both as to organization and methods of operation, may be best understood by reference to the following description, taken in conjunction with the accompanying drawings. While preferred embodiments of the present invention have been shown and described herein, it will be obvious to those skilled in the art that such embodiments are provided by way of example only. Numerous variations, changes and substitutions will now occur to those skilled in the art without departing from the invention.

DETAILED DESCRIPTION

Before explaining various embodiments of methods of controlling frequency of ultrasonic surgical instrument in detail, it should be noted that the illustrative embodiments are not limited in application or use to the details of construction and arrangement of parts of illustrated in the accompanying drawings and description. Basing on the embodiments of the invention, the embodiments obtained by those skilled in the art without departing from the invention is protected by the scope of the invention.

The purpose of the invention is to provide a method of controlling frequency of ultrasonic surgical instrument, which solves the problem of low efficiency and instability, in the case of the phase at the resonant frequency does not cross zero point.

Detailed description is illustrated below with drawings and embodiments.

Embodiment 1

Figure 1:
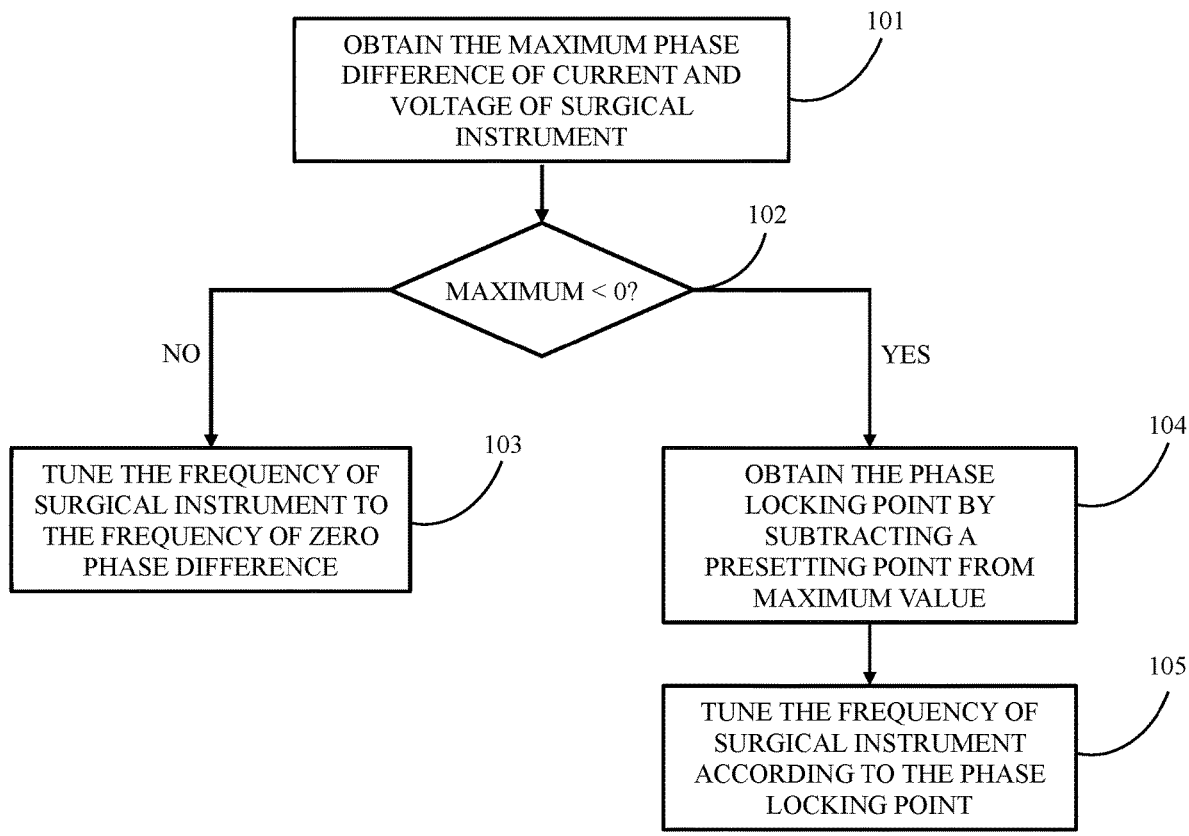
FIG. 1 illustrates a logic flow diagram of the first embodiment of controlling the frequency of surgical instrument.

FIG. 1 is the logic flow diagram of embodiment 1 of controlling frequency of surgical instrument. As shown in FIG. 1, a method of controlling frequency of ultrasonic surgical instrument, use ultrasonic scalpel as an example, includes:

Step 101, obtain the maximum phase difference of the current and voltage of surgical instrument.

Step 103, when the maximum is not less than zero, tune the frequency of surgical instrument to the frequency of zero phase difference.

When the phase difference of current and voltage is higher than zero, it indicates the surgical instrument could work at the resonant condition which means the highest efficiency.

Step 104, when the maximum value is less than zero, obtain the phase locking point by subtracting a presetting point from maximum value.

When the phase difference of current and voltage is less than zero, the zero phase set point would not work because of the non-existed zero point.

According to phase locking formula:

$$ph\_lock = ph\_now - ph\_delta \quad (1)$$

Calculate the phase locking point:
Where, ph_lock is the phase locking point, ph_now is the maximum phase difference, ph_delta is the first presetting point.

Step 105, tune the frequency of surgical instrument according to the phase locking point.

The phase locking electric circuit could achieve tuning function.

Figure 5:
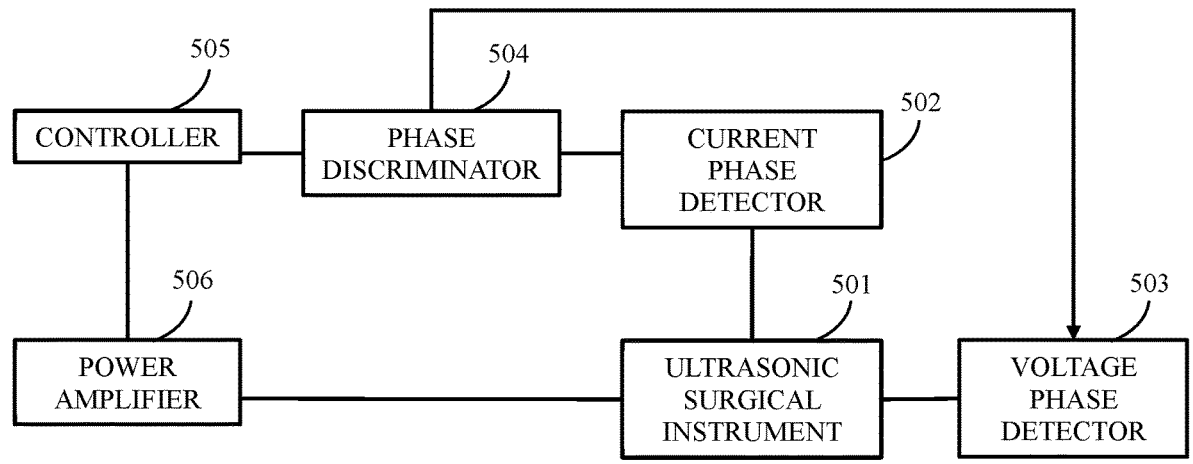
FIG. 5 is a schematic diagram of the phase locking of the surgical instrument.

FIG. 5 is the schematic diagram of phase locking, including:

Ultrasonic surgical instrument 501, current phase detector 502, voltage phase detector 503, phase discriminator 504, controller 505 and power amplifier 506.

The detected current and voltage signals of the surgical instrument 501 are fed to phase discriminator 504, which sends the result to the controller 505. The controller 505 tunes the frequency of surgical instrument according to the result. The driving signal with the corrected frequency feeds the power amplifier 506 to drive the surgical instrument 501. This is a feedback closed loop to make sure the surgical instrument 501 working at the resonant frequency.

In the case of minus maximum phase difference of current and voltage, the invention improves the efficiency and stability of the surgical instrument through lowering the phase locking point.

Embodiment 2

Figure 2:
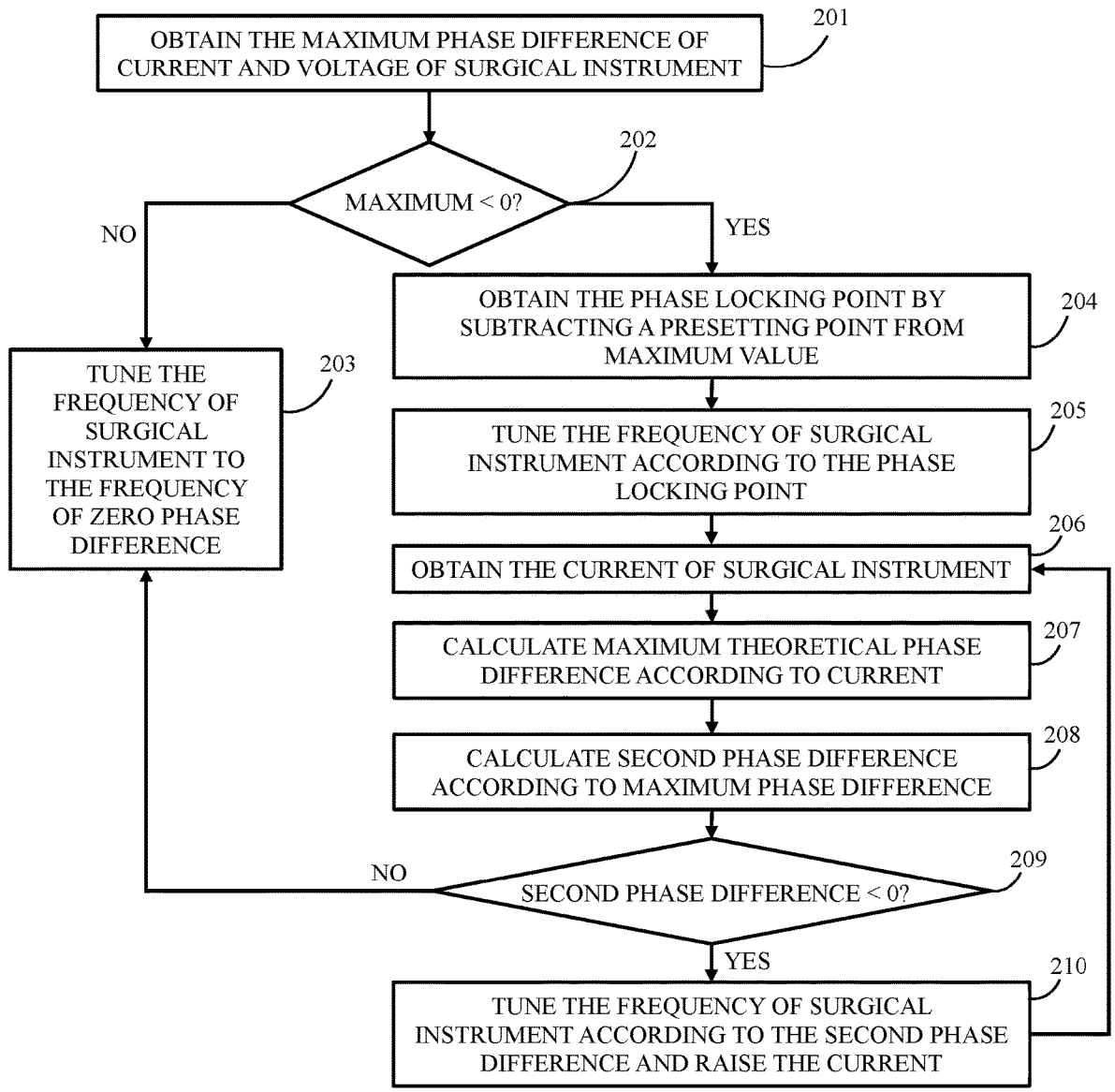
FIG. 2 illustrates a logic flow diagram of the second embodiment of controlling the frequency of surgical instrument.

FIG. 2 is the logic flow diagram of embodiment of controlling frequency of surgical instrument. As shown in FIG. 2, a method of controlling frequency of ultrasonic surgical instrument, includes:

Step 201, obtain the phase difference of the current and voltage of surgical instrument.

Step 202, determine if the maximum value is less than zero.

Step 203, when the maximum is not less than zero, tune the frequency of surgical instrument to the frequency of zero phase difference.

Step 204, when the maximum value is less than zero, obtain the phase locking point by subtracting a presetting point from maximum value.

Step 205, tune the frequency of surgical instrument according to the phase locking point.

According to phase locking formula:

$$ph\_lock = ph\_now - ph\_delta \quad (1)$$

Calculate the phase locking point:
Where, ph_lock is the phase locking point, ph_now is the maximum phase difference, ph_delta is the first presetting point. Tune the frequency of surgical instrument according to the phase locking point.

Step 206, obtain the current of surgical instrument.

Step 207, calculate the maximum phase difference according to the current.

Experimentally, in the same others conditions, when higher is the current, the bigger is the phase difference. And this could be estimated by the linear function:

$$ph\_max = a * current + b \quad (2)$$

Where, ph_max is the theoretical phase maximum value, current is the electrical current, a and b are known coefficients from experiment.

Step 208, calculate the second phase difference according to the maximum theoretical phase difference. Let ph_now=ph_max, and calculate the phase difference according the formula (1).

Step 209, determine whether the second phase difference is less than zero.

Step 210, when the second phase difference is less than zero, tune the frequency of the surgical instrument according to the second phase difference and raise the current. Specifically, tune the frequency of surgical instrument to the frequency with respect to second phase difference and raise the current, then return to Step 206.

When the second phase difference is not less than zero, do Step 203, tune the frequency of surgical instrument to zero phase difference.

In the embodiment, in the condition of minus phase difference of surgical instrument, determine the condition that if theoretical maximum phase difference is less than zero, through the current of surgical instrument and tune the frequency according to phase locking formula. This improves the efficiency and stability of surgical instrument.

Embodiment 3

Figure 3:
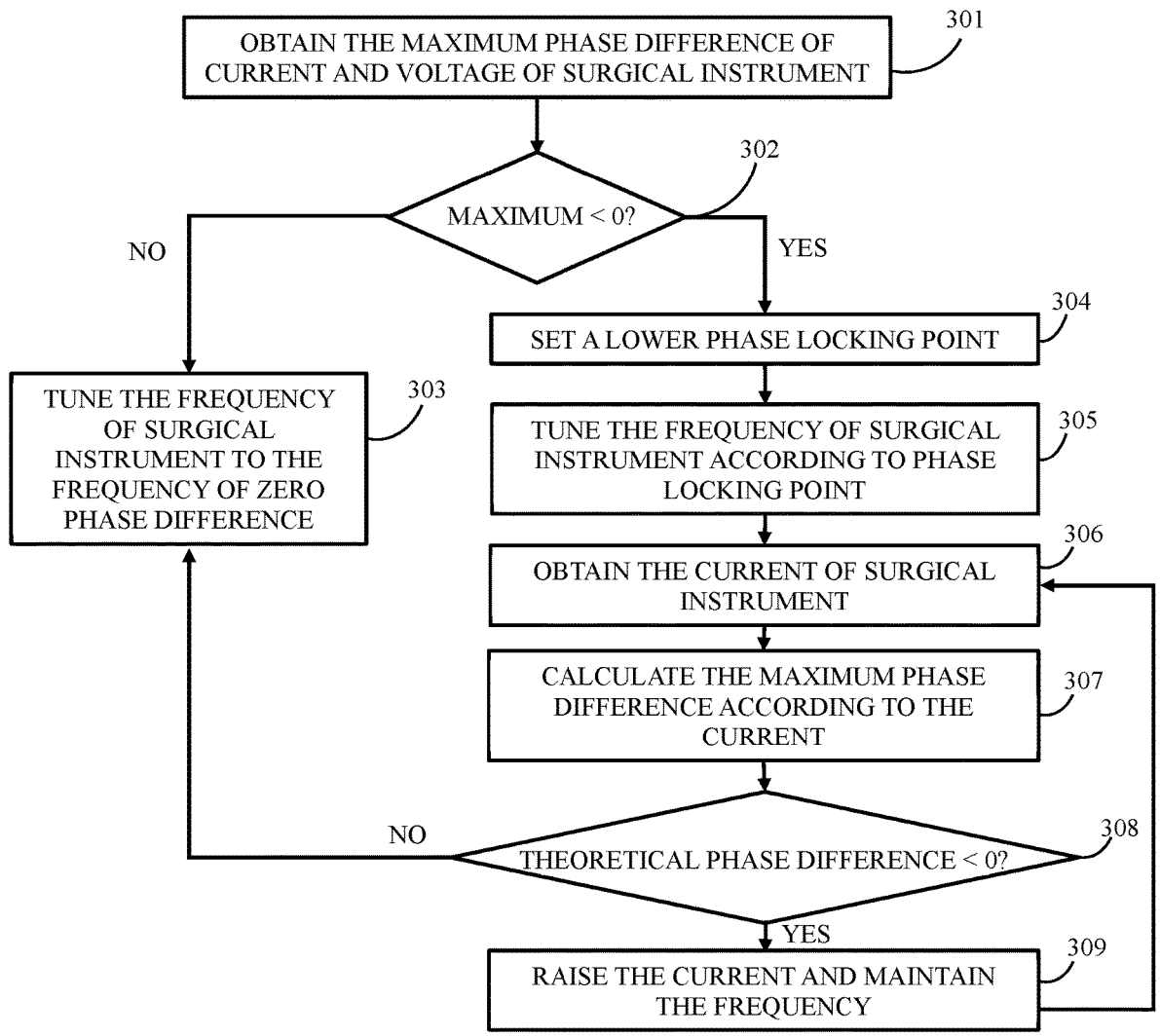
FIG. 3 illustrates a logic flow diagram of the third embodiment of controlling the frequency of surgical instrument.

FIG. 3 is the logic flow diagram of embodiment of controlling frequency of surgical instrument. As shown in FIG. 3, a method of controlling frequency of ultrasonic surgical instrument, includes:

Step 301, obtain the phase difference of the current and voltage of surgical instrument.

Step 302, determine if the maximum value is less than zero.

Step 303, when the maximum is not less than zero, tune the frequency of surgical instrument to the frequency of zero phase difference.

Step 304, when the maximum value is less than zero, set the phase locking point to a lower one, like −50 degree.

Step 305, tune the frequency of the surgical instrument according to the phase locking point.

Step 306, obtain the current of surgical instrument.

Step 307, calculate the theoretical phase difference according to the current. Specifically, calculate the maximum phase difference according to formula 2.

Step 308, determine if the maximum theoretical phase difference is less than zero.

Step 309, when the maximum theoretical phase difference is less than zero, maintains the frequency of surgical instrument, raise the current and returns to Step 306.

When the theoretical phase difference is not less than zero, tune the frequency of surgical instrument to the frequency of zero phase difference and return to Step 303.

In the embodiment, when surgical instrument works in the nonzero phase difference condition, tune the frequency of surgical instrument to the zero phase difference frequency if the maximum phase difference obtaining from current is not less than zero. When the surgical instrument works in high impedance condition which means the phase difference of resonant frequency may be less than zero, constantly forcing surgical instrument work in nonzero phase difference condition makes the low efficiency. The invention dynamically changes the set point according to the real maximum phase difference improving the efficiency of surgical instrument.

Embodiment 4

Figure 4:
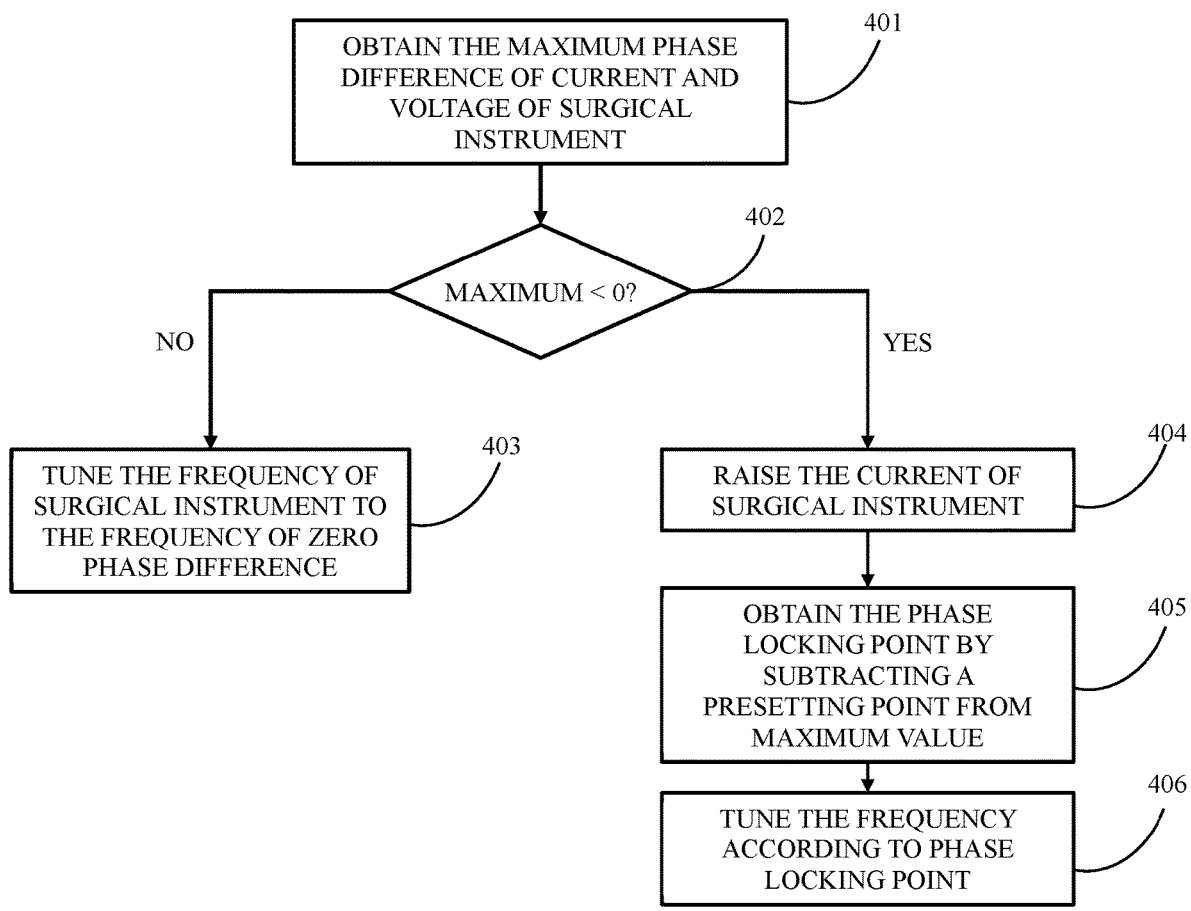
FIG. 4 illustrates a logic flow diagram of the fourth embodiment of controlling the frequency of surgical instrument.

FIG. 4 is the logic flow diagram of embodiment of controlling frequency of surgical instrument. As shown in FIG. 4, a method of controlling frequency of ultrasonic surgical instrument, includes:

Step 401, obtain the phase difference of the current and voltage of surgical instrument.

Step 402, determine if the maximum value is less than zero.

Step 403, when the maximum is not less than zero, tune the frequency of surgical instrument to the frequency of zero phase difference.

Step 404, when the maximum is less than zero, raise the current of surgical instrument. When the voltage of surgical instrument excesses nominal voltage, stop raising current.

Step 405, set a phase locking point by subtracting a presetting point from maximum value.

Step 406, tune the frequency according to phase locking point

This embodiment realizes changing the current of surgical instrument within the limit of nominal voltage by the fact that the higher current, the bigger phase difference. This improves the maximum phase difference and the efficiency of surgical instrument.

The invention offers methods of frequency controlling and solves low efficiency and instability of surgical instrument in the condition of minus phase difference.

Embodiment 5

Figure 6:
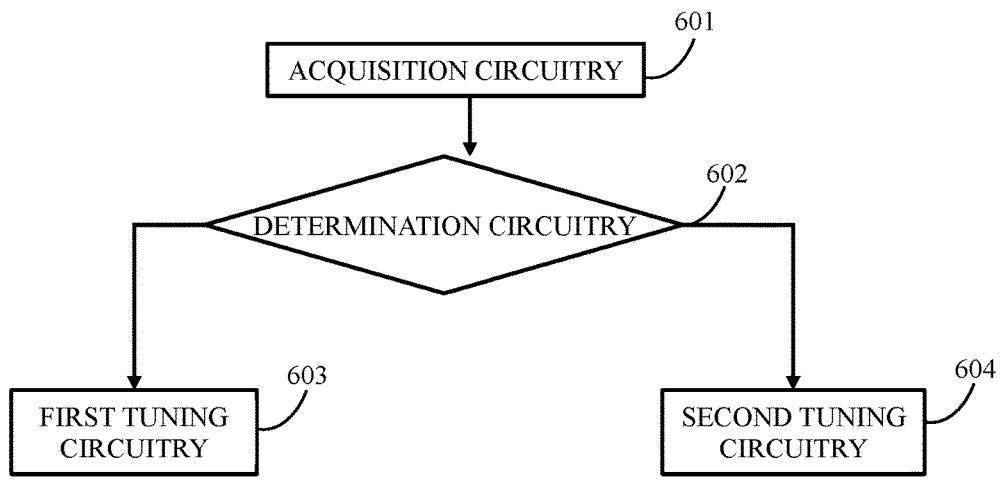
FIG. 6 is a schematic diagram of the first embodiment of the frequency controlling of the surgical instrument.

FIG. 6 is a schematic diagram of frequency controlling of surgical instrument of one embodiment. As shown in FIG. 6, the frequency controlling system of surgical instrument includes, acquisition circuitry 601, determination circuitry 602, first tuning circuitry 603, second tuning circuitry 604.

Acquisition circuitry 601, for acquiring maximum phase difference of current and voltage of surgical instrument.

Determination circuitry 602, for determining if the maximum is less than zero, obtain the first determination result.

First tuning circuitry 603, when the maximum value of first determination result is not less than zero, tune the frequency of surgical instrument to the frequency of zero phase difference.

Second tuning circuitry 604, when the maximum value of first determination is less than zero, obtain the phase locking point by subtracting a presetting point from the maximum value. Tune the frequency of the surgical instrument to phase locking point.

Embodiment 6

Figure 7:
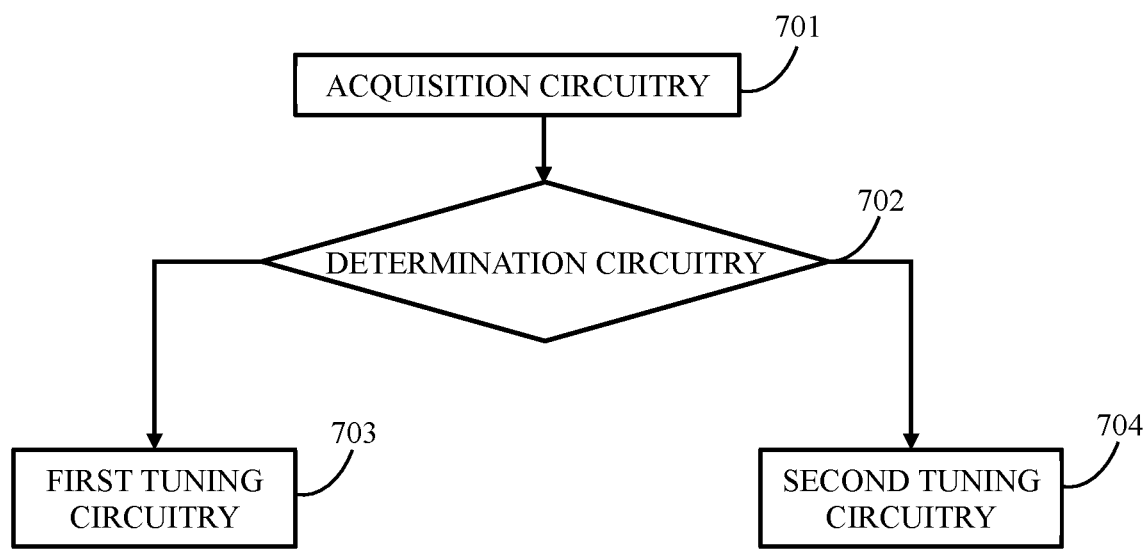
FIG. 7 is a schematic diagram of the second embodiment of the frequency controlling of the surgical instrument.

FIG. 7 is a schematic diagram of frequency controlling of surgical instrument of one embodiment. As shown in FIG. 7, the frequency controlling system of surgical instrument includes, acquisition circuitry 701, determination circuitry 702, first tuning circuitry 703, second tuning circuitry 704.

Acquisition circuitry 701, for acquiring maximum phase difference of current and voltage of surgical instrument.

Determination circuitry 702, for determining if the maximum is less than zero, obtain the fourth determination result.

The first tuning circuitry 703, when the first determination result is less than zero, raises the current of surgical instrument; monitoring the voltage, when the voltage obtained is higher than the nominal voltage of surgical instrument, stop raising; obtain the phase locking point by subtracting a presetting value from maximum value; and tune the frequency to corresponding phase locking point.

The second tuning circuitry 704, when the first determination result is not less than zero, tunes the frequency of surgical instrument to zero phase difference point.

Various embodiments are described in the invention, the difference between different embodiments are illustrated. The similarity of different embodiments could be referenced by each other.

While the invention has been particularly shown and described with reference to preferred embodiments, it could be understood by those skilled in the art that various changes in form and details may be made without departing from the scope of the invention. So, the description is not understood as the limit of the invention.

The invention claimed is:

1. A frequency control method for an ultrasonic surgical instrument, comprising:
    obtain a maximum value of a phase difference between an operating voltage and an operating current of an ultrasonic surgical instrument;
    determine whether a maximum value is less than zero and obtain a first determination result;
    when the maximum value of the first determination result is not less than zero, tuning the frequency of the ultrasonic surgical instrument to a point where the phase difference is zero; and
    when the maximum value of the first determination result is less than zero, obtain a phase locking point by subtracting a preset value from the maximum value, and tuning the frequency of ultrasonic surgical instrument according to the phase locking point.

2. The frequency control method of claim 1, wherein obtaining the phase locking point comes from subtracting a presetting value from the maximum value, including:
    according to the formula of the phase locking point:

$$ph\_lock = ph\_now - ph\_delta$$

calculating the phase locking point; and
    where: ph_lock is the phase locking point, ph_now is maximum of the phase difference, and ph_delta is the first presetting value.

3. The frequency control method of claim 2, wherein a range of ph_delta is from 0-10 degrees.

4. The frequency control method of claim 1, wherein after tuning the frequency according to the phase locking point, the method comprises:
    the obtaining a working current of the ultrasonic surgical instrument;
    calculating a maximum phase difference according to the working current; and
    tuning the frequency of the ultrasonic surgical instrument according to maximum phase difference.

5. The frequency control method of claim 4, comprising calculating a theoretical maximum phase difference according to the working current:
    according to the formula:

$$ph\_max = a * current + b \qquad (2)$$

where: the ph_max is theoretical maximum phase difference, current is the working current, and a and b are known coefficients.

6. The frequency control method of claim 5, wherein tuning the frequency of ultrasonic surgical instrument according to the maximum phase difference, includes:
    wherein: ph_max=ph_now, calculating a second phase difference according to phase locking formula;

determining if the second phase difference is less than zero and obtaining a second determination result;

when the second determination result is less than zero, tune the frequency of the ultrasonic surgical instrument to a frequency at which the second phase difference maintains; and when the second determination is not less than zero, tune the frequency of the ultrasonic surgical instrument to a frequency at which the phase difference is zero.

7. The frequency control method of claim 5, comprising tuning a working frequency of an ultrasonic surgical instrument according to the maximum phase difference, including:

determining if the theoretical phase difference is less than zero and obtaining a third determination result;

when the theoretical maximum phase difference is less than zero according to the third determination, maintaining the frequency of the ultrasonic surgical instrument; and when the theoretical maximum phase difference is not less than zero according to the third determination, tuning the frequency of the ultrasonic surgical instrument to a frequency at which phase difference is zero.

8. A method of controlling an ultrasonic surgical instrument, the method comprising:

when a maximum value of a first determination result is less than zero, increasing a current level of the ultrasonic surgical instrument;

if a corresponding voltage is higher than a limit of nominal voltage, stop increasing the current level;

obtain a phase locking point from subtracting a presetting value from the maximum value; and according to the phase locking point tuning a working current of the ultrasonic surgical instrument.

9. A control system of an ultrasonic surgical instrument, comprising:

acquirement circuitry configured to obtain a maximum value of a phase difference of current and voltage of the ultrasonic surgical instrument;

determination circuitry configured to determine if the maximum value is less than zero and obtain a first determination result;

first tuning circuitry configured to tune a frequency of the ultrasonic surgical instrument to a frequency at which the phase difference is zero, when the maximum value of the result of first determination is not less than zero; and second tuning circuitry configured to tune the frequency of ultrasonic surgical instrument to a frequency obtained from subtracting presetting value from maximum value, when the maximum value of the result of first determination is less than zero.

10. The control system of claim 9, wherein the second turning circuitry is configured to:

stop an increase of the current, when a working voltage is higher than a nominal voltage of the ultrasonic surgical instrument; and tune a frequency of the ultrasonic surgical instrument according to a phase locking point.

* * * * *

UNITED STATES PATENT AND TRADEMARK OFFICE
CERTIFICATE OF CORRECTION

PATENT NO. : 11,786,267 B2  
APPLICATION NO. : 16/635930  
DATED : October 17, 2023  
INVENTOR(S) : Fuyuan Wang et al.

Page 1 of 1

It is certified that error appears in the above-identified patent and that said Letters Patent is hereby corrected as shown below:

In the Claims

Column 8, Claim 4, Line 48:
"the obtaining a working" should read: --obtaining a working--.

Column 10, Claim 10, Line 24:
"turning circuity" should read: --tuning circuitry--.

Signed and Sealed this  
Second Day of September, 2025

Coke Morgan Stewart  
*Acting Director of the United States Patent and Trademark Office*